United States Patent
Kimura et al.

(10) Patent No.: US 6,884,768 B2
(45) Date of Patent: Apr. 26, 2005

(54) MEDICINAL COMPOSITIONS

(75) Inventors: Toshikiro Kimura, Okayama (JP); Kazutaka Higaki, Okayama (JP); Masateru Miyake, Itano-gun (JP); Takanori Minami, Itano-gun (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/480,598

(22) PCT Filed: Jun. 14, 2002

(86) PCT No.: PCT/JP02/05954

§ 371 (c)(1),
(2), (4) Date: Dec. 12, 2003

(87) PCT Pub. No.: WO02/102414

PCT Pub. Date: Dec. 27, 2002

(65) Prior Publication Data

US 2004/0161407 A1 Aug. 19, 2004

(30) Foreign Application Priority Data

Jun. 14, 2001 (JP) .................................... 2001-180373
Sep. 28, 2001 (JP) .................................... 2001-298839

(51) Int. Cl.⁷ .............................................. A61K 31/00
(52) U.S. Cl. ........................................ 514/1; 514/789
(58) Field of Search ..................................... 514/1, 789

(56) References Cited

FOREIGN PATENT DOCUMENTS

| EP | 1050310 A1 | 12/1998 |
|---|---|---|
| JP | 3-275633 A | 12/1991 |
| JP | 6-305956 A | 1/1994 |
| JP | 6-56643 A | 3/1994 |
| JP | 6-192108 A | 7/1994 |
| JP | 7-33667 A | 2/1995 |
| JP | 10-25255 A | 1/1998 |
| JP | 10-109942 A | 4/1998 |
| JP | 11-60486 A | 3/1999 |
| JP | 11-60487 A | 3/1999 |
| JP | 11-171793 A | 6/1999 |
| WO | WO 96/16671 A1 | 6/1996 |
| WO | WO 96/21448 A1 | 7/1996 |
| WO | WO 96/23490 A1 | 8/1996 |

OTHER PUBLICATIONS

Tetsuo Morishita, H. "Pylori to Shokaki Shikkan", Therapeutic Research, 1999, vol. 20, No. 8, pp. 2225 to 2227.

Miwon Son et al., Protective Effect of Taurine on Indomethacin–induce Gastric Mucosal Injury, Arch. Parm. Res., 1996, vol. 19, No. 2, pp. 85 to 90.

Toshikiro Kimura et al., Electrophysiological Approach to the Action of Taurine on Rat Gastric Mucosa, j. Pharm. Dyn., 1982, vol. 5, pp. 495 to 00.

Katsuhiro UDA, "Rat Shocho ex vivo deno Glucose Kyushu ni taisuru Polyamine no Zokyo Koka" Digestion & Absorption, 2000, vol. 23, No. 1, pp. 28–30.

*Primary Examiner*—Taofiq Solola
(74) *Attorney, Agent, or Firm*—Sughrue Mion, PLLC

(57) ABSTRACT

The present invention provides a medicinal composition comprising (1) a pharmacologically active substance, (2) a drug absorbefacient and (3) a taurine compound or a polyamine. A taurine compound has an efect of suppressing or preventing damage of the intestinal mucous membrane, and therefore adding the taurine compound to a medicinal composition containing a pharmacologically active substance and a drug absorbefacient makes it possible to suppress or prevent damage of the intestinal mucosa. A polyamine improves the absorbability of pharmacologically active substances, and therefore adding the polyamine to a medicinal composition containing a pharmacologically active substance and a drug absorbefacient makes it possible to decrease the dose of the drug absorbefacient, thereby suppressing or preventing damage of the intestinal mucosa.

10 Claims, No Drawings

MEDICINAL COMPOSITIONS

This application is a 371 of PCT/JP02/05954 filed Jun. 14, 2002

TECHNICAL FIELD

This invention relates to a medicinal composition.

BACKGROUND ART

Drug absorbefacients are generally added to medicines that contain pharmacologically active substances to improve absorption of the pharmacologically active substances (see, for example, Crit. Rev. Ther. Drug Carrier Syst., S. Muranishi, 7, p 1–33 (1990), etc.).

However, medicines that contain pharmacologically active substances and drug absorbefacients have a side effect, i.e., damaging the intestinal mucosa of the small intestine, large intestine, rectum, etc. (see, for example, E. S. Swenson, W. B. Milisen, W. Curatolo, Pharm. Res., 11(8), p 1132–1142 (1994), etc.). Such side effect is attributable to the drug absorbefacient.

To reduce the occurrence of this side effect, the amount of the drug absorbefacient has to be as small as possible. However, when the amount of drug absorbefacient is reduced, it renders a problem that its effect in promoting absorption of the pharmacologically active substance becomes weaker.

To attempt to overcome this drawback, arginine and like amino acids have been added to medicinal compositions that contain pharmacologically active substances and drug absorbefacients (see Y. Kinouchi, N. Yata, Biol. Pharm. Bull., 19(3), p 375–378 (1996)).

Addition of amino acids can prevent damage of the intestinal mucosa to some degree; however, its effect is unsatisfactory. Therefore, development of medicinal compositions that can further suppress damage of the intestinal mucosa is demanded.

It is known that polyamines have an effect in promoting maturation of the digestive tracts of infants (Japanese Unexamined Patent Publication No. 1998-262607) and that polyamines have an effect in protecting the gastric mucous membrane by preventing secretion of gastric acid (Japanese Unexamined Patent Publication No. 1983-131914). However, the above-mentioned publications nowhere teach nor suggest that polyamines improve the absorption of low molecular weight pharmacologically active substances having a molecular weight of about 1000 or less. Furthermore, no case to date has been reported that polyamines were used to improve the absorption of pharmacologically active substances in the intestinal tract.

DISCLOSURE OF THE INVENTION

An object of the present invention is to provide a medicinal composition that would cause substantially no damage to the intestinal mucosa.

The present inventors conducted extensive research and found that the above object can be achieved by adding taurine compound(s) or polyamine(s) to a medicinal composition that contains pharmacologically active substances and drug absorbefacients. In other words, the present inventors found that taurine compounds can suppress or prevent damage of the intestinal mucosa caused by the side effect of drug absorbefacient(s). The inventors also found that polyamines improve the drug absorption promoting effect of the absorbefacient(s), and therefore a combined use of a drug absorbefacient and a polyamine can reduce the amount of drug absorbefacients required. As a result, damage of the intestinal mucosa caused by the side effect of drug absorbefacients can be suppressed or prevented. The present invention was completed based on the findings.

1. The invention provides a medicinal composition comprising (1) a pharmacologically active substance, (2) a drug absorbefacient and (3) a taurine compound or a polyamine.

2. The invention provides a medicinal composition comprising a pharmacologically active substance, a drug absorbefacient and a taurine compound.

3. The invention provides a medicinal composition according to Item 2, wherein the pharmacologically active substance is at least one member selected from the group consisting of the ophylline, cilostazol, grepafloxacin, carteolol, procaterol, rebamipide, aripiprazole, 5-fluorouracil, diclofenac, cyclosporin, nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(1H)-quinolinone monomethane sulfonate, 4-(N-methyl-2-phenylethylamino)-1(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl)thiazol-4-yl]pyridine-2-carboxylic acid, mevalotin, Ioxonin, Blopress, Basen, Takepron, Pansporin, Certa, Calslot Norvasc, Lipitor, Cardenalin, Viagra, Cravit, Panaldine, Gaster, Harnal, Perdipine, Selbex, Glakay, Aricept, Lipovas, Nu-Lotan, Renivace, Flomox, Flumarin, Kefral, Zaditen, Lamisil, Epogin, Cefzon, Intal and Nivadil.

4. The invention provides a medicinal composition according to Item 2, wherein the drug absorbefacient is at least one member selected from the group consisting of alkali metal salts of bile acids and alkali metal salts of $C_{6-20}$ fatty acids.

5. The invention provides a medicinal composition according to Item 2, wherein the drug absorbefacient is at least one member selected from the group consisting of alkali metal salts of bile acids and alkali metal salts of $C_{6-13}$ fatty acids.

6. The invention provides a medicinal composition according to Item 4, wherein the drug absorbefacient is at least one member selected from the group consisting of alkali metal salts of taurocholic acid and alkali metal salts of lauric acid.

7. The invention provides a medicinal composition according to Item 2, wherein the taurine compound is taurine.

8. The invention provides an intestinal mucosa protective agent that is used in combination with a medicinal composition containing a pharmacologically active substance and a drug absorbefacient, the intestinal mucosa protective agent comprising a taurine compound.

9. The invention provides an intestinal mucosa protective agent according to Item 8, wherein the taurine compound is taurine.

10. The invention provides a method for suppressing or preventing damage of the intestinal mucosa caused by a drug absorbefacient, the method comprising adding a taurine compound to a medicinal composition that contains a pharmacologically active substance and a drug absorbefacient.

11. The invention provides a method for suppressing or preventing damage of the intestinal mucosa caused by a drug absorbefacient comprising administering a medicinal composition containing a pharmacologically active substance and a drug absorbefacient together with an intestinal mucosa protective agent comprising a taurine compound.

12. The invention provides a method for suppressing or preventing damage of the intestinal mucosa caused by administrating a medicinal composition that contains a pharmacologically active substance and a drug absorbefacient, the method comprising administering a taurine compound to a patient in need of such suppression or prevention of the damage of the intestinal mucosa.

13. The invention provides use of a taurine compound for producing an intestinal mucosa protective agent that is used in combination with a medicinal composition containing a pharmacologically active substance and a drug absorbefacient.

14. The invention provides a medicinal composition containing a pharmacologically active substance, a drug absorbefacient and a polyamine.

15. The invention provides a medicinal composition according to Item 14, wherein the drug absorbefacient is a solubilizer.

16. The invention provides a medicinal composition according to Item 14, wherein the pharmacologically active substance is at least one member selected from the group consisting of theophylline, cilostazol, grepafloxacin, carteolol, procaterol, rebamipide, aripiprazole, 5-fluorouracil, diclofenac, cyclosporin., nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(1H)-quinolinone monomethane sulfonate, 4-(N-methyl-2-phenylethylamino)-1-(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl)thiazol-4-yl]pyridine-2-carboxylic acid, mevalotin, loxonin, Blopress, Basen, Takepron, Pansporin, Certa, Calslot Norvasc, Lipitor, Cardenalin, Viagra, Cravit, Panaldine, Gaster, Harnal, Perdipine, Selbex, Glakay, Aricept, Lipovas, Nu-Lotan, Renivace, Flomox, Flumarin, Kefral, Zaditen, Lamisil, Epogin, Cefzon, Intal and Nivadil.

17. The invention provides a medicinal composition according to Item 14, wherein the drug absorbefacient is an alkali metal salt of a bile acid.

18. The invention provides a medicinal composition according to Item 17, wherein the drug absorbefacient is at least one member selected from the group consisting of alkali metal salts of taurocholic acid and alkali metal salts of taurodeoxycholic acid.

19. The invention provides a medicinal composition according to Item 14, wherein the polyamine is spermine.

20. The invention provides a drug absorption enhancer that is used in combination with a medicinal composition containing a pharmacologically active substance and a drug absorbefacient, the drug absorption enhancer comprising a polyamine.

21. The invention provides a drug absorption enhancer according to Item 20, wherein the drug absorbefacient is a solubilizer.

22. The invention provides a drug absorption enhancer according to Item 20 or 21, wherein the polyamine is spermine.

23. The invention provides an intestinal mucosa protective agent that is used in combination with a medicinal composition containing a pharmacologically active substance and a drug absorbefacient, the intestinal mucosa protective agent comprising a polyamine.

24. The invention provides an intestinal mucosa protective agent according to Item 23, wherein the drug absorbefacient is a solubilizer.

25. The invention provides an intestinal mucosa protective agent according to Item 23 or 24, wherein the polyamine is spermine.

26. The invention provides a method for improving absorption of a pharmacologically active substance, the method comprising adding a polyamine to a medicinal composition containing the pharmacologically active substance and a drug absorbefacient.

27. The invention provides a method for suppressing or preventing damage of the intestinal mucosa, the method comprising adding a polyamine to a medicinal composition containing a pharmacologically active substance and a drug absorbefacient.

28. The invention provides a method for improving absorption of a pharmacologically active substance, the method comprising using a medicinal composition containing the pharmacologically active substance and a drug absorbefacient in combination with a drug absorption enhancer comprising a polyamine.

29. The invention provides a method for suppressing or preventing damage of the intestinal mucosa, the method comprising using a medicinal composition containing a pharmacologically active substance and a drug absorbefacient in combination with a drug absorption enhancer comprising a polyamine.

30. The invention provides a method for suppressing or preventing damage of the intestinal mucosa caused by administration of a medicinal composition containing a pharmacologically active substance and a drug absorbefacient, the method comprising administering a polyamine to reduce the dose of the drug absorbefacient to a patient in need of suppression or prevention of damage of the intestinal mucosa.

31. The invention provides use of a polyamine for producing a drug absorption enhancer used in combination with a medicinal composition containing a pharmacologically active substance and a drug absorbefacient.

32. The invention provides a medicinal composition that contains a poorly soluble pharmacologically active substance and polyamine, but does not contain a drug absorbefacient.

33. The invention provides a medicinal composition according to Item 32, wherein the drug absorbefacient is a solubilizer.

34. The invention provides a medicinal composition according to Item 32, wherein the poorly soluble pharmacologically active substance is at least one member selected from the group consisting of cilostazol, rebamipide, cyclosporin and nifedipine.

35. The invention provides a medicinal composition according to Item 32, wherein the polyamine is spermine.

36. The invention provides a drug absorption improvement agent that is used in combination with a medicinal composition that contains a poorly soluble pharmacologically active substance but does not contain a drug absorbefacient, and that contains polyamine.

37. The invention provides a method for improving absorption of a pharmacologically active substance by adding a polyamine to a medicinal composition that contains a poorly soluble pharmacologically active substance but does not contain a drug absorbefacient.

38. The invention provides a method for improving absorption of a poorly soluble pharmacologically active substance by administering a polyamine to a patient in need of administration of a poorly soluble pharmacologically active substance.

39. The invention provides use of a polyamine for producing a drug absorption improvement agent that is used in combination with a medicinal composition containing a poorly soluble pharmacologically active substance but not containing a drug absorbefacient.

The medicinal composition of the present invention comprises (1) a pharmacologically active substance, (2) a drug absorbefacient and (3) a taurine compound or polyamine. In the present specification, a drug absorbefacient is a compound that promotes absorption of pharmacologically active substances.

Taurine Compound-Containing Medicinal Composition

Medicinal compositions that contain taurine compounds are described below.

The medicinal composition of the invention contains pharmacologically active substance(s), drug absorbefacient(s) and taurine compound(s).

The pharmacologically active substances are not limited as long as they can be absorbed through the intestinal mucosa, and a wide range of known ones can be used. Examples of usable pharmacologically active substances include those generally used in various kinds of pharmaceutical preparations, such as, respiratory drugs, gastrointestinal drugs, circulatory drugs, the central nerves system drugs, the peripheral nerves system drugs, antibiotics, chemotherapeutics, antitumor agents, platelet aggregation inhibitors, anti-allergy agents, vitamin preparations, diagnostic preparations, etc.

Specific examples of such pharmacologically active substances include theophylline, cilostazol, grepafloxacin, carteolol, procaterol, rebamipide, aripiprazole, 5-fluorouracil, diclofenac, cyclosporin, nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(1H)-quinolinone monomethane sulfonate, 4-(N-methyl-2-phenylethylamino)-1-(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl)thiazol-4-yl]pyridine-2-carboxylic acid, mevalotin, loxonin, Blopress, Basen, Takepron, Pansporin, Certa, Calslot Norvasc, Lipitor, Cardenalin, Viagra, Cravit, Panaldine, Gaster, Harnal, Perdipine, Selbex, Glakay, Aricept, Lipovas, Nu-Lotan, Renivace, Flomox, Flumarin, Kefral, Zaditen, Lamisil, Epogin, Cefzon, Intal, Nivadil,. etc.

Among these, preferable pharmacologically active substances include, for example, theophylline, cilostazol, grepafloxacin, carteolol, procaterol, rebamipide, aripiprazole, 5-fluorouracil, diclofenac, cyclosporin, nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(1H)-quinolinone monomethane sulfonate, 4-(N-methyl-2-phenylethylamino)-1-(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl)thiazol-4-yl]pyridine-2-carboxylic acid, etc.

Specific examples of especially preferable pharmacologically active substances include theophylline, cilostazol, grepafloxacin, carteolol, procaterol, rebamipide, aripiprazole, 5-fluorouracil, diclofenac, cyclosporin, nifedipine, phenol red, etc.

These pharmacologically active substances can be used singly or in a combination of two or more.

There is no restriction on the drug absorbefacients as long as they promote absorption of pharmacologically active substances and a wide range of those known can be used. Examples of such drug absorbefacients include bile salts, medium-chain fatty acid salts, long-chain fatty acid salts, surfactants, cyclodextrins, alkyl saccharides, chelating agents, alkylcarbamates, sorbitan fatty acid esters, etc.

Examples of bile salts include alkali metal salts of bile acid, such as cholic acid, glycocholic acid, taurocholic acid, deoxycholic acid, chenodeoxycholic acid, taurodeoxycholic acid, etc. Specific examples thereof include sodium cholate, sodium glycocholate, sodium taurocholate, sodium deoxycholate, sodium chenodeoxycholate, sodium taurodeoxycholate, etc.

Examples of medium-chain fatty acid salts include salts (in particular, alkali metal salts) of fatty acids having 6–13 carbon atoms, specifically, alkali metal salts (sodium salt, potassium salt, etc.) of caproic acid, caprylic acid, lauric acid, lauryl sulfate, etc.

Examples of long-chain fatty acid salts include salts (in particular, alkali metal salts) of fatty acids having 14–20 carbon atoms, specifically, alkali metal salts (sodium salt, potassium salt, etc.) of myristic acid, palmitic acid, stearic acid, oleic acid, linoleic acid, linolenic acid, arachidonic acid, etc.

Examples of surfactants include anionic surfactants, nonionic surfactants, etc. Specific examples of nonionic surfactants include glycerol monostearate, capric triglyceride, lauric triglyceride, glyceryl monoundecylenate, tetraglyceryl pentastearate and like glycerides of medium-chain fatty acids, polysorbate 80, polyoxyethylene hydrogenated castor oil, polyoxyethylene castor oil, polyoxyethylene lanolin, polyoxyethylene lanolin alcohols, polyoxyethylene lauryl ether, polyoxyethylene cetyl ether, etc.

Examples of cyclodextrins include dimethyl-β-cyclodextrin, hydroxypropyl-β-cyclodextrin, sulfobutyl ether-β-cyclodextrin, etc.

Examples of alkyl saccharides include carboxyfluorescein, lauryl maltoside, etc.

Examples of chelating agents include EDTA and like polyaminocarboxylic acids; citric acid and like oxycarboxylic acids; dimethylglyoxime and like oximes, etc.

Examples of alkylcarbamates include $C_1$–$C_4$ alkylcarbamates, specifically methylcarbamate, ethylcarbamate, butylcarbamate, etc.

Examples of sorbitan fatty acid esters include sorbitan monolaurate, sorbitan monopalmitate, sorbitan sesquistearate, sorbitan sesquioleate, etc.

Preferable drug absorbefacients include bile salts, medium-chain fatty acid salts, long-chain fatty acid salts, etc.

More preferable drug absorbefacients include bile salts, medium-chain fatty acid salts, etc.

These drug absorbefacients are used singly or in a combination of two or more.

In the present invention, it is essential to add a taurine compound to the above-described composition that contains a pharmacologically active substance and a drug absorbefacient. Taurine compounds have an effect to protect the intestinal mucosa.

In the present invention, the taurine compounds include, in addition to taurine, N-acylated taurines (for example, N—$C_{2-24}$-acylated taurine, etc.), N-alkylated taurines (for example, N—$C_{2-24}$-alkylated taurine, etc.), salts of taurine (for example, sodium, potassium and like alkali metal salts, alkaline earth metal salts, ammonium salts, organic amine salts, etc.), etc.

Preferable taurine compounds include taurine, etc.

These taurine compounds are used singly or in a combination of two or more.

There is no limitation to the amount of the taurine compound; however, considering the effect of protecting the intestinal mucosa, economy, etc., the amount of the taurine compound is generally 0.001–100 parts by weight, preferably 0.05–100 parts by weight, more preferably 0.05–50 parts by weight, and particularly preferably 0.1–10 parts by weight, based on one part by weight of drug absorbefacient.

There is no restriction on the amount of the pharmacologically active substance and drug absorbefacient contained in the composition, and they may be general contents.

There is no limitation to the amount of the drug absorbefacient; however, considering the effect of improving drug absorption, it is recommended that the amount thereof be generally 0.01–1000 parts by weight, preferably 0.05–100 parts by weight, more preferably 0.1–50 parts by weight, and most preferably 0.1–10 parts by weight, based on one part by weight of pharmacologically active substance.

The medicinal composition of the invention is generally made into a pharmaceutical preparation by mixing the above-mentioned pharmacologically active substance, drug absorbefacient and taurine compound with various kinds of carriers, such as excipients, binders, disintegrators, etc.

A wide range of known excipients may be used, including, for example, lactose, sucrose, glucose and like various kinds of saccharides; potato starch, wheat starch, cornstarch and like various kinds of starches; crystalline cellulose and like various kinds of celluloses; anhydrous calcium hydrogen phosphate, calcium carbonate and like various kinds of inorganic salts, etc.

Various kinds of known binders can be used, including crystalline cellulose, pullulan, gum arabic, sodium alginate, polyvinyl pyrrolidone, macrogol, etc.

A wide range of known disintegrators can be used, including carboxymethyl cellulose, calcium carboxymethyl cellulose, hydroxypropyl cellulose, hydroxypropyl starch, starch, sodium alginate, etc.

There is no limitation to the form of the medicinal composition of the invention, and it may take, for example, tablet, capsule, granule and various other forms. The taurine compounds have the effect of suppressing or preventing damage of the intestinal mucosa caused by drug absorbefaciencts, and it is therefore preferable that the pharmaceutical preparation of the invention be in the form of a pharmaceutical preparation that can be disintegrated in the intestinal tract such as the small intestine, large intestine, rectum, etc.

It is recommended that the dosage of the taurine compound be generally 0.2–1000 mg, preferably 0.2–100 mg and more preferably 2–50 mg, per day per kg of body weight.

The present invention provides a method for suppressing or preventing damage of the intestinal mucosa caused by a drug absorbefacient, the method comprising adding a taurine compound to a medicinal composition containing a pharmacologically active substance and the drug absorbefacient.

Taurine Compound-Containing Intestinal Mucosa Protective Agent

As described above, taurine compounds protect the intestinal mucosa. Therefore, the present invention provides an intestinal mucosa protective agent comprising a taurine compound.

In the present invention, the taurine compounds include, in addition to taurine, N-acylated taurines (for example, N—$C_{2-24}$-acylated taurine, etc.), N-alkylated taurines (for example, N—$C_{2-24}$-alkylated taurine, etc.), salts of taurine (for example, sodium, potassium and like alkali metal salts, alkaline earth metal salts, ammonium salt, organic amine salts, etc.), etc.

There is no limitation to the amount of taurine compound contained in the intestinal mucosa protective agent of the invention, and it may be suitably selected from a wide range.

Such taurine compounds are used singly or in a combination of two or more.

The amount of the taurine compound in a pharmaceutical preparation is not limited and may be suitably selected from a wide range. It is recommended that the amount of taurine compound in the pharmaceutical preparation be, for example, generally 0.01–80 wt. %, preferably 0.1–50 wt. % and more preferably 1–20 wt. %.

The intestinal mucosa protective agent may contain the above-described drug absorbefaciencts together with the taurine compound. When the amount of drug absorbefacient contained in the intestinal mucosa protective agent increases, it is possible to proportionally reduce the amount of drug absorbefacient contained in the medicinal composition that comprises a pharmacologically active substance and the drug absorbefacient, and that is used in combination with the intestinal mucosa protective agent.

The intestinal mucosa protective agent of the invention is generally made into a pharmaceutical preparation by being added with a taurine compound together with excipients, binders, disintegrators and like carriers.

As excipients, various kinds of known ones can be used, such as lactose, sucrose, glucose and like saccharides; potato starch, wheat starch, cornstarch and like starches; crystalline cellulose and like celluloses; anhydrous calcium hydrogen phosphate, calcium carbonate and like inorganic salts, etc.

Various kinds of known binders can be used in the invention, for example, crystalline cellulose, pullulan, gum arabic, sodium alginate, polyvinyl pyrrolidone, macrogol, etc.

A wide range of known disintegrators can be used in the invention, for example, carboxymethyl cellulose, calcium carboxymethyl cellulose, hydroxypropyl cellulose, hydroxypropyl starch, starch, sodium alginate, etc.

There is no limitation to the form of the intestinal mucosa protective agent of the invention and it can take, for example, tablet, capsule, granule and various other forms. Since taurine compounds have the effect of suppressing or preventing damage of the intestinal mucosa caused by drug absorbefacient, and it is therefore preferable that the pharmaceutical preparation of the invention be used as an intestinal tract disintegrating pharmaceutical preparation that dissolves in the small intestine, large intestine, rectum, etc.

The intestinal mucosa protective agent of the invention is used in combination with a medicinal composition containing a pharmacologically active substance and a drug absorbefacient.

When the intestinal mucosa protective agent is used in combination with the medicinal composition, both may be administered simultaneously. It is also possible to administer the intestinal mucosa protective agent and then after an interval the medicinal composition, or to administer the medicinal composition and then the intestinal mucosa protective agent in this order.

It is recommended that the dosage of the taurine compound be generally 0.2–1000 mg, preferably 0.2–100 mg and more preferably 2–50 mg, per day per kg of body weight.

The invention provides a method for suppressing or preventing damage of the intestinal mucosa caused by a drug absorbefacient, wherein a medicinal composition containing a pharmacologically active substance and a drug absorbefacient is used in combination with an intestinal mucosa protective agent containing a taurine compound.

The present invention provides a method for suppressing or preventing damage of the intestinal mucosa caused by administrating a medicinal composition that contains a pharmacologically active substance and a drug absorbefacient, the method comprising administering a taurine compound to a patient in need of such suppression or prevention of damage of the intestinal mucosa.

The present invention provides use of a taurine compound to produce an intestinal mucosa protective agent that is used with a medicinal composition containing a pharmacologically active substance and a drug absorbefacient.

Polyamine-Containing Medicinal Composition A

Medicinal compositions that contain polyamine(s) are explained below.

The medicinal composition of the invention comprises a pharmacologically active substance, a drug absorbefacient and a polyamine. The polyamine enhances the effects of the drug absorbefacient.

There is no limitation to the pharmacologically active substances and various known kinds can be used as long as they can be absorbed through the intestinal mucosa. Examples of such pharmacologically active substances include generally used pharmacologically active substances, such as, respiratory drugs, gastrointestinal drugs, circulatory drugs, the central nerves system drugs, the peripheral nerves system drugs, antibiotics, chemotherapeutics, antitumor agents, platelet aggregation inhibitors, anti-allergy agents, vitamin preparations, diagnostic preparations, etc.

Specific examples of such pharmacologically active substances include theophylline, cilostazol, grepafloxacin, carteolol, procaterol, rebamipide, aripiprazole, 5-fluorouracil, diclofenac, cyclosporin, nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(1H)-quinolinone monomethane sulfonate, 4-(N-methyl-2-phenylethylamino)-1-(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl)thiazol-4-yl]pyridine-2-carboxylic acid, mevalotin, loxonin, Blopress, Basen, Takepron, Pansporin, Certa, Calslot Norvasc, Lipitor, Cardenalin, Viagra, Cravit, Panaldine, Gaster, Harnal, Perdipine, Selbex, Glakay, Aricept, Lipovas, Nu-Lotan, Renivace, Flomox, Flumarin, Kefral, Zaditen, Lamisil, Epogin, Cefzon, Intal, Nivadil, etc.

Preferable pharmacologically active substances include, for example, theophylline, cilostazol, grepafloxacin, carteolol, procaterol, rebamipide, aripiprazole, 5-fluorouracil, diclofenac, cyclosporin, nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(1H)-quinolinone monomethane sulfonate, 4-(N-methyl-2-phenylethylamino)-1-(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl)thiazol-4-yl]pyridine-2-carboxylic acid, etc.

Specifically preferable pharmacologically active substances include theophylline, cilostazol, grepafloxacin, carteolol, procaterol, rebamipide, aripiprazole, 5-fluorouracil, diclofenac, cyclosporin, nifedipine, phenol red, etc.

These pharmacologically active substances can be used singly or in a combination of two or more.

Among the drug absorbefacients, some compounds function to promote dissolution of the above-mentioned pharmacologically active substances, and therefore it is possible to use poorly soluble pharmacologically active substances as the pharmacologically active substance of the invention. In this specification, compounds which are drug absorbefacients and function as promoters for dissolving the pharmacologically active substances are referred to as "solubilizers".

Herein, a poorly soluble pharmacologically active substance means a pharmacologically active substance having a solubility in water of no more than 10 mg/ml. For example, drugs whose solubility is in the categories of "extremely hardly soluble" and "almost not soluble" defined in the Japanese Pharmacopoeia 13$^{th}$ edition correspond to the poorly soluble pharmacologically active substances.

Among the above-mentioned pharmacologically active substances, cilostazol, rebamipide, aripiprazole, cyclosporin and nifedipine are poorly soluble pharmacologically active substances. Among these poorly soluble pharmacologically active substances, rebamipide, cyclosporin and nifedipine are pharmacologically active substances having a low absorption. Herein, pharmacologically active substances having a low absorption are those whose absorption rate is less than 40%. The definition of absorption rate and the measuring method thereof are described in, for example, Walter E., Janich S., Roessler B. J., Hilfinger J. H., Amidon G., 1996; J. Pharm. Sci. 85, 1070–1076.

There is no limitation to drug absorbefacients as long as they are compounds that can enhance the absorption of the above-mentioned pharmacologically active substances, and various kinds of known absorbefacients can be used. Specifically, the drug absorbefacients exemplified under the title of taurine compound-containing medicinal composition can be used. Among these, the compounds that have the effect of aiding dissolution of pharmacologically active substances and can be used as solubilizers are, for example, bile salts, medium-chain fatty acid salts, long-chain fatty acid salts, surfactants, cyclodextrins, etc.

As bile salts, for example, alkali metal salts of cholic acid, glycocholic acid, taurocholic acid, deoxycholic acid, chenodeoxycholic acid, taurodeoxycholic acid and like bile acids can be exemplified. Specific examples thereof include sodium cholate, sodium glycocholate, sodium taurocholate, sodium deoxycholate, sodium chenodeoxycholate, sodium taurodeoxycholate, etc.

Examples of the medium-chain fatty acid salts include salts (in particular, alkali metal salts) of fatty acids having 6–13 carbon atoms, specifically, alkali metal salts (sodium salt, potassium salt, etc.) of caproic acid, caprylic acid, lauric acid, lauryl sulfate, etc.

Examples of long-chain fatty acid salts include salts (in particular, alkali metal salts) of fatty acids having 14–20 carbon atoms, specifically, alkali metal salts (sodium salt, potassium salt, etc.) of myristic acid, palmitic acid, stearic acid, oleic acid, linoleic acid, linolenic acid, arachidonic acid, etc.

Examples of surfactants include anionic surfactants, nonionic surfactants, etc. Specific examples of nonionic surfactants include such as glycenol monostearate, capric triglyceride, lauric triglyceride, glyceryl monoundecylenate, tetraglyceryl pentastearate and like glycerides of medium-chain fatty acids, polysorbate 80, polyoxyethylene hydrogenated castor oil, polyoxyethylene castor oil, polyoxyethylene lanolin, polyoxyethylene lanolin alcohols, polyoxyethylene lauryl ether, polyoxyethylene cetyl ether, etc.

Examples of cyclodextrins include dimethyl-β-cyclodextrin, hydroxypropyl-β-cyclodextrin, sulfobutyl ether-β-cyclodextrin, etc.

Preferable drug absorbefacients are, for example, bile salts, medium-chain fatty acid salts, long-chain fatty acid salts, etc.

More preferable drug absorbefacients are, for example, bile salts, medium-chain fatty acid salts, etc.

These drug absorbefacients can be used singly or in a combination of two or more.

In the present invention, it is essential to add polyamine(s) to the compositions containing a pharmacologically active substance and a drug absorbefacient (solubilizer).

The polyamines are not limited and a wide range of known polyamines can be used. Specific examples of polyamines include spermine, spermidine, putrescine, cadaverine, 1,3-diaminopropane, caldine, homospermidine, aminopropylcadaverine, thermine, thermospermine, canavalmine, aminopentylnorspermine, N,N'-bis(aminopropyl)cadaverine, caldopentamine, homocaldopentamine, caldohexamine, etc.

Preferable polyamines include spermine, spermidine, putrescine, cadaverine, thermine, thermospermine, canavalmine, aminopentylnorspermine, N,N'-bis(aminopropyl)cadaverine, caldopentamine, homocaldopentamine, caldohexamine, etc.

More preferable polyamines include spermine, spermidine, putrescine, cadaverine, etc.

These polyamines can be used singly or in a combination of two or more.

The amount of polyamines is not limited; however, considering the effects of enhancing absorption, economy, etc., it is recommended the that the amount thereof be generally 0.001–5000 wt. %, preferably 0.005–1000 wt. %, more preferably 0.05–1000 wt. %, and still more preferably 0.1–500 wt. %, based on one part by weight of the drug absorbefacient.

There is no limitation to the amounts of the pharmacologically active substance and the drug absorbefacient contained in the medicinal composition of the invention and therefore they may be used in usual amounts. However, the polyamines have the effect of promoting absorption of the pharmacologically active substances from the intestinal tract or have the effect of enhancing the pharmacologically active substances absorption promoting effect of the drug absorbefacient, and accordingly the amount of the drug absorbefacient can be reduced. For example, it is recommended that an effective amount of a pharmacologically active substance be used and the drug absorbefacient be used in an amount of 0.01–1000 wt. %, preferably 0.05–500 wt. %, more preferably 0.1–500 wt. %, and particularly preferably 0.1–100 wt. %, based on the pharmacologically active substance.

The medicinal composition of the invention is generally made into a pharmaceutical preparation by mixing the above-mentioned pharmacologically active substance, drug absorbefacient and polyamine with various kinds of carriers, such as excipients, binders, disintegrators, etc.

A wide range of known excipients may be used, including lactose, sucrose, glucose and like various kinds of saccharides, potato starch, wheat starch, cornstarch and like various kinds of starches; crystalline cellulose and like various kinds of celluloses., anhydrous calcium hydrogen phosphate, calcium carbonate and like various kinds of inorganic salts, etc.

Various kinds of known binders can be used, for example, crystalline cellulose, pullulan, gum arabic, sodium alginate, polyvinyl pyrrolidone, macrogol, etc.

A wide range of known disintegrators can be used, including carboxymethyl cellulose, calcium carboxymethyl cellulose, hydroxypropyl cellulose, hydroxypropyl starch, starch, sodium alginate, etc.

There is no limitation to the form of the medicinal composition of the invention and it can take, for example, tablet, capsule, granule, liquid, suppository and various other forms. Generally, the medicinal composition of the invention is orally administered. Since the pharmacologically active substances contained in the medicinal composition of the invention are absorbed through the intestinal mucosa, it is preferable that the pharmaceutical preparation of the invention be in the form of a pharmaceutical preparation that can be disintegrated in the intestinal tract such as the small intestine, large intestine, rectum, etc.

The dosage of the polyamine is generally 0.0001–100 mg, preferably 0.005–20 mg, more preferably 0.05–20 mg, and still more preferably 0.5–20 mg, per day per kg of body weight.

The invention provides a method for improving absorption of the pharmacologically active substance by adding a polyamine to a medicinal composition containing the pharmacologically active substance and a drug absorbefacient.

The invention provides a method for suppressing or preventing damage of the intestinal mucosa by adding a polyamine to a medicinal composition containing a pharmacologically active substance and a drug absorbefacient.

Polyamines improve absorption of pharmacologically active substances. Therefore, the amount of drug absorbefacient in the medicinal composition can be reduced. Accordingly, it is possible to supress or prevent damage of the intestinal mucosa caused by the drug absorbefacients.

The invention provides a method for suppressing or preventing damage of the intestinal mucosa caused by administering a medicinal composition containing a pharmacologically active substance and a drug absorbefacient, the method comprising administering a polyamine to a patient in need of such suppression or prevention of damage of the intestinal mucosa, to thereby reduce the dose of the drug absorbefacient.

Polyamine-Containing Drug Absorption Enhancer

As mentioned above, the polyamines enhance the pharmacologically active substance absorption promoting effect of the drug absorbefacients. Therefore, the present invention provides a drug absorption enhancer comprising a polyamine.

The polyamines are not limited and various known ones can be used. Specific examples of polyamines include spermine, spermidine, putrescine, cadaverine, 1,3-diaminopropane, caldine, homospermidine, aminopropylcadaverine, thermine, thermospermine, canavalmine, aminopentylnorspermine, N,N'-bis (aminopropyl)cadaverine, caldopentamine, homocaldopentamine, caldohexamine, etc.

Preferable polyamines include spermine, spermidine, putrescine, cadaverine, thermine, thermospermine, canavalmine, aminopentylnorspermine, N,N'-bis(aminopropyl)cadaverine, caldopentamine, homocaldopentamine, caldohexamine, etc.

More preferable polyamines include spermine, spermidine, putrescine, cadaverine, etc.

These polyamines can be used singly or in a combination of two or more.

There is no limitation to the amount of the polyamine used and it may be suitably selected from a wide range. It is recommended that the amount of the polyamine in the pharmaceutical preparation be, for example, generally 0.01–80 wt. %, preferably 0.1–50 wt. %, and more preferably 1–20 wt. %.

The drug absorption enhancer of the invention is generally made into a pharmaceutical preparation by mixing the polyamine(s) with various kinds of carriers such as excipients, binders, disintegrators, etc.

A wide range of known excipients may be used in the invention, including lactose, sucrose, glucose and like various kinds of saccharides; potato starch, wheat starch, cornstarch and like various kinds of starches; crystalline cellulose and like various kinds of celluloses; anhydrous calcium hydrogen phosphate, calcium carbonate and like various kinds of inorganic salts, etc.

Various kinds of known binders can be used, including crystalline cellulose, pullulan, gum arabic, sodium alginate, polyvinyl pyrrolidone, macrogol, etc.

A wide range of known disintegrators can be used, including carboxymethyl cellulose, calcium carboxymethyl cellulose, hydroxypropyl cellulose, hydroxypropyl starch, starch, sodium alginate, etc.

There is no limitation to the form of the drug absorption enhancer of the invention and it can take, for example, tablet, capsule, granule, liquid, suppository and various other forms. Generally, the medicinal composition of the invention is orally administered. Since polyamines are effective for suppressing or preventing damage of the intestinal mucosa caused by the drug absorbefacients, it is preferable that the drug absorption enhancer of the invention be in the form of a pharmaceutical preparation that can be disintegrated in the intestinal tract such as the small intestine, large intestine, rectum, etc.

The drug absorption enhancer of the invention is used in combination with a medicinal composition containing a pharmacologically active substance and a drug absorbefacient.

When the drug absorption enhancer is used in combination with the medicinal composition, both may be administered simultaneously. It is also possible to administer the drug absorption enhancer and then the medicinal composition after an interval, or to administer the medicinal composition and then the drug absorption enhancer in this order.

The dosage of the polyamine(s) is, generally 0.0001–100 mg, preferably 0.005–20 mg, more preferably 0.05–20 mg, and still more preferably 0.5–20 mg, per day per kg of body weight.

The invention provides use of a polyamine to produce a drug absorption enhancer to be used in combination with a medicinal composition containing a pharmacologically active substance and a drug absorbefacient.

Polyamine-Containing Intestinal Mucosa Protective Agent

As mentioned above, the polyamines enhance the pharmacologically active substance absorption promoting effect of the drug absorbefacients. Therefore, it is possible to reduce the amount of drug absorbefacient used. This makes it possible to suppress or prevent damage of intestinal mucosa caused by the side effects of the drug absorbefacient. Therefore, the invention provides an intestinal mucosa protective agent comprising a polyamine.

The polyamines are not limited and various known ones can be used. Specific examples of polyamines include spermine, spermidine, putrescine, cadaverine, 1,3-diaminopropane, caldine, homospermidine, aminopropylcadaverine, thermine, thermospermine, canavalmine, aminopentylnorspermine, N,N'-bis(aminopropyl)cadaverine, caldopentamine, homocaldopentamine, caldohexamine, etc.

Preferable polyamines include spermine, spermidine, putrescine, cadaverine, thermine, thermospermine, canavalmine, aminopentylnorspermine, N,N'-bis(aminopropyl)cadaverine, caldopentamine, homocaldopentamine, caldohexamine, etc.

More preferable polyamines include spermine, spermidine, putrescine, cadaverine, etc.

These polyamines are used singly or in a combination of two or more.

There is no limitation to the amount of the polyamine used and it may be suitably selected from a wide range. For example, it is recommended that the amount of the polyamine in the pharmaceutical preparation be generally 0.01–80 wt. %, preferably 0.1–50 wt. %, and more preferably 1–20 wt. %.

The intestinal mucosa protective agent of the invention is generally made into a pharmaceutical preparation by mixing polyamine(s) with excipients, binders, disintegrators and various like carriers.

A wide range of known excipients may be used, including, for example, lactose, sucrose, glucose and like various kinds of saccharides; potato starch, wheat starch, cornstarch and like various kinds of starches; crystalline cellulose and like various kinds of celluloses; anhydrous calcium hydrogen phosphate, calcium carbonate and like various kinds of inorganic salts, etc.

Various kinds of known binders can be used, for example, crystalline cellulose, pullulan, gum arabic, sodium alginate, polyvinyl pyrrolidone, macrogol, etc.

A wide range of known disintegrators can be used, including carboxymethyl cellulose, calcium carboxymethyl cellulose, hydroxypropyl cellulose, hydroxypropyl starch, starch, sodium alginate, etc.

There is no limitation to the form of the intestinal mucosa protective agent of the invention and it can take, for example, tablet, capsule, granule, liquid, suppository and various other forms. Generally, the medicinal composition of the invention is orally administered. Since polyamines are effective for suppressing or preventing damage of the intestinal mucosa caused by the drug absorbefacients, it is preferable that the intestinal mucosa protective agent of the invention be in the form of a pharmaceutical preparation that can be disintegrated in the intestinal tract such as the small intestine, large intestine, rectum, etc.

The intestinal mucosa protective agent of the invention is used in combination with a medicinal composition containing a pharmacologically active substance and a drug absorbefacient.

When the intestinal mucosa protective agent is used in combination with the medicinal composition, both may be administered simultaneously. It is also possible to administer the intestinal mucosa protective agent and after an interval the medicinal composition, or to administer the medicinal composition and then the intestinal mucosa protective agent.

The dosage of the polyamine(s) is generally 0.0001–100 mg, preferably 0.005–20 mg, more preferably 0.05–20 mg, and still more preferably 0.5–20 mg, per day per kg of body weight.

Polyamines improve absorption of pharmacologically active substances. Therefore, the amount of drug absorbefacient in the medicinal composition can be reduced. Accordingly, it is possible to suppress or prevent damage of the intestinal mucosa caused by the drug absorbefacient.

The invention provides a method for suppressing or preventing damage of the intestinal mucosa caused by administering a medicinal composition containing a pharmacologically active substance and a drug absorbefacient, the method comprising administering a polyamine to a patient in need of such suppression or prevention of damage of the intestinal mucosa to reduce the dose of drug absorbefacient.

Polyamine-Containing Medicinal Composition B

Medicinal compositions that contain polyamine(s) are described below.

Polyamines have the effect of enhancing absorption of pharmacologically active substances. Therefore, the invention provides a medicinal composition that comprises poorly soluble pharmacologically active substance(s) and polyamine(s), but does not contain a drug absorbefacient (solubilizer).

Herein, a poorly soluble pharmacologically active substance means a pharmacologically active substance having a solubility in water of no more than 10 mg/ml. For example, drugs whose solubility is in the categories of "extremely hardly soluble" and "almost not soluble" defined in the Japanese Pharmacopoeia $13^{th}$ edition correspond to the poorly soluble pharmacologically active substances.

The poorly soluble pharmacologically active substances are not limited and various known ones can be used as long as they can be absorbed from the intestinal mucosa. Examples of usable pharmacologically active substances include pharmacologically active substances generally used in respiratory drugs, gastrointestinal drugs, circulatory drugs, the central nerves system drugs, the peripheral nerves system drugs, antibiotics, chemotherapeutics, antitumor agents, platelet aggregation inhibitors, anti-allergy agents, vitamin preparations, diagnostic preparations, etc.

Specific examples of such poorly soluble pharmacologically active substances include cilostazol, rebamipide, aripiprazole, cyclosporin and nifedipine. Among these poorly soluble pharmacologically active substances, rebamipide, cyclosporin and nifedipine are pharmacologically active substances having a low absorption. Herein, pharmacologically active substances having a low absorption are those whose absorption rate is less than 40%. The definition of absorption rate and the measuring method thereof are described in, for example, Walter E., Janich S., Roessler B. J., Hilfinger J. H., Amidon G., 1996; J. Pharm. Sci. 85, 1070–1076.

These poorly soluble pharmacologically active substances can be used singly or in a combination of two or more.

The polyamines are not limited and a wide range of known ones can be used. Specific examples of polyamines include spermine, spermidine, putrescine, cadaverine, 1,3-diaminopropane, caldine, homospermidine, aminopropylcadaverine, thermine, thermospermine, canavalmine, aminopentylnorspermine, N,N'-bis(aminopropyl)cadaverine, caldopentamine, homocaldopentamine, caldohexamine, etc.

Preferable polyamines include spermine, spermidine, putrescine, cadaverine, thermine, thermospermine, canavalmine, aminopentylnorspermine, N,N'-bis(aminopropyl)cadaverine, caldopentamine, homocaldopentamine, caldohexamine, etc.

More preferable polyamines include spermine, spermidine, putrescine, cadaverine, etc.

These polyamines can be used singly or in a combination of two or more.

There is no limitation to the amount of the polyamine; however, considering the effects of enhancing absorption, economy, etc., it is recommended that the amount thereof be generally 0.01–10000 wt. %, preferably 0.05–1000 wt. %, more preferably 0.1–500 wt. %, and most preferably 1–100 wt %, based on one part by weight of the drug absorbefacient.

There is no limitation to the amount of pharmacologically active substance contained in the medicinal composition of the invention, and therefore it may be used in an usual amount. For example, the amount is generally 0.01–80 wt. %, preferably 0.1–50 wt. % and more preferably 1–20 wt. %.

The medicinal composition of the invention is generally made into a pharmaceutical preparation by mixing the above-mentioned pharmacologically active substances and polyamine(s) with various kinds of carriers such as excipients, binders, disintegrators, etc.

A wide range of known excipients may be used, for example, lactose, sucrose, glucose and like various kinds of saccharides; potato starch, wheat starch, cornstarch and like various kinds of starches; crystalline cellulose and like various kinds of celluloses; anhydrous calcium hydrogen phosphate, calcium carbonate and like various kinds of inorganic salts, etc.

Various kinds of known binders can be used, for example, crystalline cellulose, pullulan, gum arabic, sodium alginate, polyvinyl pyrrolidone, macrogol, etc.

A wide range of known disintegrators can be used, including carboxymethyl cellulose, calcium carboxymethyl cellulose, hydroxypropyl cellulose, hydroxypropyl starch, starch, sodium alginate, etc.

There is no limitation to the form of the medicinal composition of the invention and it can take, for example, tablet, capsule, granule, liquid, suppository and various other forms. Generally, the medicinal composition of the invention is orally administered. Since the pharmacologically active substances contained in the medicinal composition of the invention are absorbed from the intestinal mucosa, it is preferable that the pharmaceutical preparation of the invention be in the form of a pharmaceutical preparation that can be disintegrated in the intestinal tract such as the small intestine, large intestine, rectum, etc.

The dosage of the polyamine(s) is generally 0.0001–100 mg, preferably 0.005–20 mg, more preferably 0.05–20 mg, and still more preferably 0.5–20 mg, per day per kg of body weight.

Polyamine-Containing Drug Absorption Improvement Agent

The above-mentioned polyamines improve absorption of pharmacologically active substances as described above. Therefore, the invention provides a drug absorption improvement agent comprising a polyamine.

The polyamines are not limited and various known ones can be used. Specific examples of polyamines include spermine, spermidine, putrescine, cadaverine, 1,3-diaminopropane, caldine, homospermidine, aminopropylcadaverine, thermine, thermospermine, canavalmine, aminopentylnorspermine, N,N'-bis(aminopropyl)cadaverine, caldopentamine, homocaldopentamine, caldohexamine, etc.

Preferable polyamines include spermine, spermidine, putrescine, cadaverine, thermine, thermospermine, canavalmine, aminopentylnorspermine, N,N'-bis(aminopropyl)cadaverine, caldopentamine, homocaldopentamine, caldohexamine, etc.

More preferable polyamines include spermine, spermidine, putrescine, cadaverine, etc.

These polyamines can be used singly or in a combination of two or more.

There is no limitation to the amount of the polyamine and it may be suitably selected from a wide range. It is recommended that the amount of the polyamine in the pharmaceutical preparation be, for example, generally 0.01–80 wt. %, preferably 0.1–50 wt. %, and more preferably 1–20 wt. %.

The drug absorption improvement agent of the invention is generally made into a pharmaceutical preparation by mixing the polyamine(s) with various kinds of carriers such as excipients, binders, disintegrators, etc.

A wide range of known excipients may be used, for example, lactose, sucrose, glucose and like various kinds of saccharides; potato starch, wheat starch, cornstarch and like various kinds of starches; crystalline cellulose and like various kinds of celluloses; anhydrous calcium hydrogen phosphate, calcium carbonate and like various kinds of inorganic salts, etc.

Various kinds of known binders can be used, including crystalline cellulose, pullulan, gum arabic, sodium alginate, polyvinyl pyrrolidone, macrogol, etc.

A wide range of known disintegrators can be used, including carboxymethyl cellulose, calcium carboxymethyl cellulose, hydroxypropyl cellulose, hydroxypropyl starch, starch, sodium alginate, etc.

There is no limitation to the form of the drug absorption improvement agent of the invention and it can take, for example, tablet, capsule, granule, liquid, suppository and various other forms. Generally, the medicinal composition of the invention is orally administered. Since the medicinal composition of the invention is absorbed in the intestinal tract, it is preferable that the polyamine-containing drug be in the form of a pharmaceutical preparation that can be disintegrated in the intestinal tract such as the small intestine, large intestine, rectum, etc.

The drug absorption improvement agent of the invention is used in combination with a medicinal composition that contains a poorly soluble pharmacologically active substance.

Herein, the poorly soluble pharmacologically active substances are the same as those described above.

When the drug absorption improvement agent and the medicinal composition are used in a combined manner, both can be administered simultaneously. It is also possible to administer the drug absorption improvement agent first and then medicinal composition after an interval, or the medicinal composition first and then the drug absorption improvement agent.

The dosage of the polyamine(s) is, generally 0.0001–100 mg, preferably 0.005–20 mg, more preferably 0.05–20 mg, and still more preferably 0.5–20 mg, per day per kg of body weight.

The invention provides a method for improving absorption of pharmacologically active substances by adding polyamine(s) to a medicinal composition that contains a poorly soluble pharmacologically active substance but does not contain a drug absorbefacient.

The invention provides a method for improving absorption of poorly soluble pharmacologically active substances by administering polyamine(s) to patients in need of administration of poorly soluble pharmacologically active substances.

The invention provides use of polyamines to produce a drug absorption improvement agent that is used in combination with a medicinal composition that contains a poorly soluble pharmacologically active substance but does not contain a drug absorbefacient.

EFFECT OF THE INVENTION

The medicinal composition of the invention that contains a taurine compound is excellent in that it causes substantially no damage to the intestinal mucosa while maintaining the drug absorption promoting effect.

The use of the medicinal composition that contains a pharmacologically active substance and a drug absorbefacient in combination with the intestinal mucosa protective agent comprising a taurine compound makes it possible to suppress or prevent damage of the intestinal mucosa caused by the drug absorbefacient.

The medicinal composition of the invention that contains a polyamine has an excellent ability to suppress damage of the intestinal mucosa and additionally to significantly improve the drug absorption promoting effect.

The use of a medicinal composition that contains a pharmacologically active substance and a drug absorbefacient in combination with a drug absorption enhancer comprising a polyamine makes it possible to significantly enhance the effect of the drug absorbefacient.

The use of a medicinal composition that contains a pharmacologically active substance and a drug absorbefacient in combination with a drug absorption enhancer that contains a polyamine makes it possible to reduce the amount of the drug absorbefacient, with the result that damage of the intestinal mucosa can be suppressed or prevented.

Because polyamines have the effect of enhancing absorption of pharmacologically active substances from the intestinal tract, it is possible to reduce the amount of drug absorbefacient used and, as a result, damage of the intestinal mucosa can be suppressed.

BEST MODE FOR CARRYING OUT THE INVENTION

Hereinafter, the present invention will be explained in more detail with reference to Preparation Examples and Test Examples. However, the scope of the present invention is not limited to the Preparation Examples below.

PREPARATION EXAMPLE T-1

Cilostazol bulk powder (800 g) ground by a jet mill and having an average particle diameter of about 2 $\mu$m, 800 g of hydroxypropylmethylcellulose, 224 g of D-mannitol, 60 g of sodium laurylsulfate (drug absorbefacient) and 60 g of taurine (product of TOKYO KASEI KOGYO CO., LTD.) were mixed. The mixture was subjected to wet granulation by adding 900 g of purified water, dried and then sieved. To the sieved granules, 16 g of magnesium stearate (lubricant) was added and mixed. Using a punch having a diameter of 6.5 mm, the mixture was then subjected to tablet compression in such a manner that the weight of one tablet became 98 mg, producing tablets having a cilostazol content of 40 mg/tablet.

The resulting tablets were placed into capsules in such a manner that each capsule held 5 tablets, producing multiple-unit type capsules each having cilostazol content of 200 mg per capsule.

PREPARATION EXAMPLE T-2

Polyvinyl alcohol (3.3 g), 10 g of mannitol, 2 g of sodium laurylsulfate and 3 g of taurine (product of TOKYO KASEI KOGYO CO., LTD.) were dissolved in 106 g of water. To the obtained solution, 20 g of cilostazol bulk powder ground by a jet mill and having an average particle diameter of about 3 μm was dispersed and dissolved, and the obtained solution was subjected to spray drying to obtain a cilostazol powder preparation.

PREPARATION EXAMPLE T-3 (TABLET)

Rebamipide (20 g), 20 g of sodium laurate (product of TOKYO KASEI KOGYO CO., LTD.), 50 g of taurine (product of TOKYO KASEI KOGYO CO., LTD.), 100 g of cornstarch (product of NIHON SHOKUHIN KAKO CO., LTD) and 100 g of crystalline cellulose (product of Asahi Kasei Corporation) were mixed and 0.5 g of magnesium stearate (product of TAIHEI CHEMICALS LIMITED) was further added. The obtained mixture was subjected to tablet compression using a punch having a diameter of 8.5 mm, producing tablets each weighting 290.5 mg.

PREPARATION EXAMPLE T-4 (TABLET)

Rebamipide (20 g), 20 g of sodium laurate (product of TOKYO KASEI KOGYO CO., LTD.), 100 g of taurine (product of TOKYO KASEI KOGYO CO., LTD.), 100 g of cornstarch (product of NIHON SHOKUHIN KAKO CO., LTD) and 100 g of crystalline cellulose (product of Asahi Kasei Corporation) were mixed and 0.5 g of magnesium stearate (product of TAIHEI CHEMICALS LIMITED) was further added. The obtained mixture was subjected to tablet compression using a punch having a diameter of 9.0 mm, producing tablets each weighting 340.5 mg.

PREPARATION EXAMPLE T-5 (GRANULE)

Rebamipide (20 g), 20 g of sodium laurate (product of TOKYO KASEI KOGYO CO., LTD.), 50 g of taurine (product of TOKYO KASEI KOGYO CO., LTD.), 100 g of cornstarch (product of NIHON SHOKUHIN KAKO CO., LTD) and 100 g of crystalline cellulose (product of Asahi Kasei Corporation) were fed into a kneader (product of OKADA SEIKO CO., LTD., product name of NSK-150) and mixed, and 200 g of water was then added thereto to obtain a kneaded product. This kneaded product was subjected to extrusion granulation using an extrusion granulator equipped with a dome shaped die having openings of 0.8 mm (product of Fuji Paudal Co., Ltd., product name of Dome Gran DG-L1). The extrudates were spheronized into spherical shape using a spheronizer (product of Fuji Paudal Co., Ltd., product name of Marumerizer QJ-400). The thus obtained sieved pellets were dried, producing granules.

PREPARATION EXAMPLE T-6 (GRANULE)

Onto the granules obtained in Preparation Example T-5, a coating solution containing 6% hydroxypropylmethylcellulose, 2% polyethylene glycol, 1% talc and 1% titanium oxide was sprayed, producing coated granules.

PREPARATION EXAMPLE T-7 (SOLUTION)

A mixture of 20 g of rebamipide, 20 g of sodium laurate (product of TOKYO KASEI KOGYO CO., LTD.), 50 g of taurine (product of TOKYO KASEI KOGYO CO., LTD.), 100 g of hydroxypropylmethylcellulose (product of Shin-Etsu Chemical Co., Ltd.), 100 g of water and 0.5 ml of 2N-sodium hydroxide solution was heated at 37° C. and mixed until it became homogeneous, giving a solution.

PREPARATION EXAMPLE T-8 (SOLUTION)

A mixture of 20 g of rebamipide, 20 g of sodium laurate (product of TOKYO KASEI KOGYO CO., LTD.), 100 g of taurine (product of TOKYO KASEI KOGYO CO., LTD.), 100 g of hydroxypropylmethylcellulose (product of Shin-Etsu Chemical Co., Ltd.), 100 g of water and 0.5 ml of 2N-sodium hydroxide solution was heated at 37° C. and mixed until it became homogeneous, giving a solution.

PREPARATION EXAMPLE T-9 (SUPPOSITORY)

A mixture of 20 g of rebamipide, 150 g of Witepsol W-35 (product of SASOL Germany GmbH), 20 g of sodium laurate (product of TOKYO KASEI KOGYO CO., LTD.) and 50 g of taurine (product of TOKYO KASEI KOGYO CO., LTD.) was heated at 37° C. and mixed until the mixture became homogeneous. The thus obtained solution was placed in a mold to produce suppositories.

PREPARATION EXAMPLE T-10 (SUPPOSITORY)

A mixture of 20 g of rebamipide, 150 g of Witepsol H-15 (product of SASOL Germany GmbH), 20 g of sodium laurate (product of TOKYO KASEI KOGYO CO., LTD.) and 50 g of taurine (product of TOKYO KASEI KOGYO CO., LTD.) was heated at 37° C. and mixed until the mixture became homogeneous. The thus obtained solution was placed in a mold to produce suppositories.

PREPARATION EXAMPLE T-11 (SUPPOSITORY)

A mixture of 20 g of rebamipide, 150 g of polyethylene glycol 1000 (product of Sigma-Aldrich Corporation), 200 g of polyethylene glycol 4000 (product of Sigma-Aldrich Corporation), 100 g of water, 20 g of sodium laurate (product of TOKYO KASEI KOGYO CO., LTD.) and 50 g of taurine (product of TOKYO KASEI KOGYO CO., LTD.) was heated at 37° C. and mixed until the mixture became homogeneous. The thus obtained solution was placed in a mold to produce suppositories.

PREPARATION EXAMPLE T-12 (SUPPOSITORY)

A mixture of 20 g of rebamipide, 150 g of polyethylene glycol 1000 (product of Sigma-Aldrich Corporation), 200 g of polyethylene glycol 8000 (product of Sigma-Aldrich Corporation), 100 g of water, 20 g of sodium laurate (product of TOKYO KASEI KOGYO CO., LTD.) and 50 g of taurine (product of TOKYO KASEI KOGYO CO., LTD.) was heated at 37° C. and mixed until the mixture became homogeneous. The thus obtained solution was placed in a mold to produce suppositories.

PREPARATION EXAMPLE T-13 (TABLET)

Taurine (product of TOKYO KASEI KOGYO CO., LTD.) (50 g), 100 g of cornstarch (product of NIHON SHOKUHIN KAKO CO., LTD) and,100 g of crystalline cellulose (product of Asahi Kasei Corporation) were mixed and 0.5 g of magnesium stearate (product of TAIHEI CHEMICALS LIMITED) was then further added. The obtained mixture was subjected to tablet compression using a punch having a diameter of 8.5 mm, producing tablets each weighting 250.5 mg.

PREPARATION EXAMPLE T-14 (GRANULE)

Taurine (product of TOKYO KASEI KOGYO CO., LTD.) (50 g), 100 g of cornstarch (product of NIHON SHOKUHIN KAKO CO., LTD) and 100 g of crystalline cellulose (product of Asahi Kasei Corporation) were fed into a kneader (product of OKADA SEIKO CO., LTD., product name of NSK-150) and mixed, and then 200 g of water was added thereto to obtain a kneaded product. This kneaded product was subjected to extrusion granulation using an extrusion granulator equipped with a dome shaped die having openings of 0.8 mm (product of Fuji Paudal Co., Ltd., product name of Dome Gran DG-L1). The extrudates were spheronized into spherical shape using a spheronizer (product of Fuji Paudal Co., Ltd., product name of Marumerizer QJ-400). The thus obtained pellets were dried, producing granules.

PREPARATION EXAMPLE T-15 (SOLUTION)

A mixture of 50 g of taurine (product of TOKYO KASEI KOGYO CO., LTD.), 100 g of hydroxypropylmethylcellulose (product of Shin-Etsu Chemical Co., Ltd.)., 100 g of water and 0.5 ml of 2N-sodium hydroxide solution was heated at 37° C. and mixed until it became homogeneous, giving a solution.

PREPARATION EXAMPLE T-16 (SUPPOSITORY)

A mixture of 150 g of Witepsol W-35 (product of SASOL Germany GmbH) and 50 g of taurine (product of TOKYO KASEI KOGYO CO., LTD.) was heated at 37° C. and mixed until it became homogeneous, giving a solution. The thus obtained solution was placed in a mold to produce suppositories.

PREPARATION EXAMPLE T-17 (SUPPOSITORY)

A mixture of 150 g of polyethylene glycol 1000 (product of Sigma-Aldrich Corporation), 200 g of polyethylene glycol 4000 (product of Sigma-Aldrich Corporation), 100 g of water and 50 g of taurine (product of TOKYO KASEI KOGYO CO., LTD.) was heated at 37° C. and mixed until it became homogeneous, giving a solution. The thus obtained solution was placed in a mold to produce suppositories.

PREPARATION EXAMPLE T-18 (SUPPOSITORY)

A mixture of 150 g of polyethylene glycol 1000 (product of Sigma-Aldrich Corporation), 200 g of polyethylene glycol 8000 (product of Sigma-Aldrich Corporation), 100 g of water and 50 g of taurine (product of TOKYO KASEI KOGYO CO., LTD.) was heated at 37° C. and mixed until it became homogeneous, giving a solution. The thus obtained solution was placed in a mold to produce suppositories.

TEST EXAMPLE T-1

Using phenol red (PR) as a model compound for testing absorption, the following 9 kinds of solutions were prepared:

Solution TA (Control 1)

PR was added to tris-hydrochloric acid buffer solution (pH 7.4) until the concentration of PR became 250 $\mu$M, giving Solution TA.

Solution TB (Control 2)

PR and sodium laurate (drug absorbefacient) were added to tris-hydrochloric acid buffer solution (pH 7.4) so that the concentration of PR became 250 $\mu$M and that of sodium laurate became 10 mM, giving Solution TB.

SOLUTION TC (COMPARATIVE EXAMPLE 1)

PR, sodium laurate (drug absorbefacient) and arginine were added to tris-hydrochloric acid buffer solution (pH 7.4) so that the concentration of PR became 250 $\mu$M, that of sodium laurate became 10 mM and that of arginine became 10 mM, giving Solution TC.

SOLUTION TD (COMPARATIVE EXAMPLE 2)

PR, sodium laurate (drug absorbefacient) and leucine were added to tris-hydrochloric acid buffer solution (pH 7.4) so that the concentration of PR became 250 $\mu$M, that of sodium laurate became 10 mM and that of leucine became 10 mM, giving Solution TD.

SOLUTION TE (COMPARATIVE EXAMPLE 3)

PR, sodium laurate (drug absorbefacient) and glycine were added to tris-hydrochloric acid buffer solution (pH 7.4) so that the concentration of PR became 250 $\mu$M, that of sodium laurate became 10 mM and that of glycine became 10 mM, giving Solution TE.

Solution TF (Control 3)

PR and sodium taurocholate (drug absorbefacient) were added to tris-hydrochloric acid buffer solution (pH 7.4) so that the concentration of PR became 250 $\mu$M and that of sodium taurocholate became 20 mM, giving Solution TF.

SOLUTION TG (COMPARATIVE EXAMPLE 4)

PR, sodium taurocholate (drug absorbefacient) and arginine were added to tris-hydrochloric acid buffer solution (pH 7.4) so that the concentration of PR became 250 $\mu$M, that of sodium taurocholate became 20 mM and that of arginine became 20 mM, giving Solution TG.

SOLUTION TH (EXAMPLE 1)

PR, sodium laurate (drug absorbefacient) and taurine were added to tris-hydrochloric acid buffer solution (pH 7.4) so that the concentration of PR became 250 $\mu$M, that of sodium laurate became 10 mM and that of taurine became 10 mM, giving Solution TH.

SOLUTION TI (EXAMPLE 2)

PR, sodium taurocholate (drug absorbefacient) and taurine were added to tris-hydrochloric acid buffer solution (pH 7.4) so that the concentration of PR became 250 $\mu$M, that of sodium taurocholate became 20 mM and that of taurine became 20 mM, giving Solution TI.

(1) Test Conducted Using Sodium Laurate as a Drug Absorbefacient

Wistar male rats (body weight of about 250 g) were used as test animals. In the upper part of the large intestine of each rat, a 10 cm loop was made and 1 ml of one of solutions TA to TE and TH prepared above was administered. The solution remaining in the loop 1.5 hours after the administration was collected.

The residual amounts of PR in the collected solutions were measured to obtain the absorption rate (%) of the PR absorbed in the large intestine of each rat.

The amounts of phospholipid (PL) and lactate dehydrogenase (LDH), markers of damage to the large intestines of the rats, were measured using the collected solutions.

The fact that the phospholipid (PL) and lactate dehydrogenase (LDH) are markers of the intestinal mucosa damage is disclosed in, for example, E. S. Swenson, W. B. Milisen, W. Curatolo, Pharm. Res., 11(8), p. 1132–1142(1994); U. Werner, T. Kissel, and M. Reers, Pharm. Res., 13(8), p. 1219–1227(1996); S. Choksakulnimitr, S. Masuda, H. Tokuda, Y. Takakura, M. Hashida, J. Control. Rel., 34, p. 233–241(1995); etc.

Table 1 shows the results.

TABLE 1

| Solution | PR absorption rate (%) | Amount of PL released (μg) | Amount of LDH released (IU) |
|---|---|---|---|
| TA (Control 1) | 9.2 ± 0.6 | 29.6 ± 6.0 | 0.52 ± 0.10 |
| TB (Control 2) | 36.7 ± 1.5 | 165.6 ± 24.3 | 1.95 ± 0.24 |
| TC (Comparative Example 1) | 43.3 ± 4.2 | 66.0 ± 18.3 | 1.68 ± 0.86 |
| TD (Comparative Example 2) | 37.0 ± 1.7 | 78.2 ± 4.0 | 1.53 ± 0.13 |
| TE (Comparative Example 3) | 39.8 ± 2.0 | 86.5 ± 3.3 | 2.00 ± 0.11 |
| TH (Example 1) | 33.1 ± 3.2 | 44.6 ± 5.2 | 0.55 ± 0.05 |

The following becomes clear from Table 1:

Compared to Solution TA (Control 1) that did not contain sodium laurate (drug absorbefacient), Solution TB (Control 2) that contained sodium laurate (drug absorbefacient) exhibited an improved absorption rate of PR; however, the amounts of PL and LDH released were significantly increased and the large intestines of rats were damaged.

In Solutions TC to TE (Comparative Examples 1–3) that contained sodium laurate (drug absorbefacient) and an amino acid, the amount of PL released was reduced to some degree; however, the amount of LDH released was not reduced, and therefore damage of the large intestine of the rats was not suppressed.

In Solution TH (Example 1) that contained sodium laurate (drug absorbefacient) and taurine, the amounts of released PL and LDH were remarkably suppressed without sacrificing absorption rate of. PR, and therefore the damage of the large intestine of the rats was greatly supressed.

(2) Test Conducted Using Sodium Taurocholate as a Drug Absorbefacient

Wistar male rats (body weight of about 250 g) were used as test animals. In the upper part of the large intestine of each rat, a 10 cm loop was made and 1 ml of the solution (Solution TA, TF, TG or TI) prepared above was administered. The solution remaining in the loop 1.5 hours after the administration was collected.

The residual amount of PR in the collected solution was measured to obtain the absorption rate (%) of the PR absorbed in the large intestine of each rat.

The amounts of phospholipid (PL) and lactate dehydrogenase (LDH), markers of the damage to the large intestines of the rats, were measured using the collected solutions.

Table 2 shows the results.

TABLE 2

| Solution | PR absorption rate (%) | Amount of PL released (μg) | Amount of LDH released (IU) |
|---|---|---|---|
| TA (Control 1) | 9.2 ± 0.6 | 29.6 ± 6.0 | 0.52 ± 0.10 |
| TF (Control 3) | 31.5 ± 1.9 | 195.1 ± 19.5 | 1.90 ± 0.05 |
| TG (Comparative Example 4) | 30.9 ± 2.6 | 168.3 ± 17.3 | 1.88 ± 0.04 |
| TI (Example 2) | 34.2 ± 3.6 | 77.6 ± 13.5 | 1.47 ± 0.07 |

Table 2 shows the following facts:

Compared to Solution TA (Control 1) that did not contain sodium taurocholate (drug absorbefacient), Solution TF (Control 3) that contained sodium taurocholate (drug absorbefacient) improved the absorption rate of PR; however, the amounts of released PL and LDH significantly increased, and therefore the large intestine of the rats were damaged.

Solution TG (Comparative Example 4) that contained sodium taurocholate (drug absorbefacient) and amino acid (arginine) did not decrease the absorption rate of PR; however, it did not significantly suppress the amounts of released PL and LDH, and therefore could not suppress damage of the large intestines of the rats.

Solution TI (Example 2) that contained sodium taurocholate (drug absorbefacient) and taurine remarkably suppressed the amounts of released PL and LDH without decreasing the absorption rate of PR, and therefore prevented damage of the large intestines of the rats.

TEST EXAMPLE T-2

Using rebamipide (product name of Mucosta, product of Otsuka Pharmaceutical Co., Ltd.) as a model compound for testing absorption, the following three kinds of solutions were prepared.

Solution TJ (Control 4)

Rebamipide and hydroxypropylmethylcellulose (product name of TC-5E, product of Shin-Etsu Chemical Co., Ltd.) were added to tris-hydrochloric acid buffer solution (pH 7.4) so that the concentration of rebamipide became 2.0 mg/ml and that of hydroxypropylmethylcellulose became 1 wt. %; and 2N—NaOH was added thereto dropwise so as to convert the mixture into a solution state, giving Solution TJ.

Solution TK (Control 5)

Rebamipide, hydroxypropylmethylcellulose and sodium laurate (solubilizer) were added to tris-hydrochloric acid buffer solution (pH 7.4) so that the concentration of rebamipide became 2.0 mg/ml, that of hydroxypropylmethylcellulose became 1 wt. % and that of sodium laurate became 3.6 mM; and 2N—NaOH was added thereto dropwise so as to convert the mixture into a solution state, giving Solution TK.

SOLUTION TL (EXAMPLE 3)

Rebamipide, hydroxypropylmethylcellulose, sodium laurate (solubilizer) and taurine were added to tris-hydrochloric acid buffer solution (pH 7.4) so that the concentration of rebamipide became 2.0 mg/ml, that of hydroxypropylmethylcellulose became 1 wt. %, that of sodium laurate became 3.6 mM and that of taurine became 20 mM; and 2N—NaOH was added thereto dropwise so as to convert the mixture into a solution state, giving Solution TL.

SD male rats (body weight of about 250 g) were used as test animals. In the upper part of the large intestine of a rat, a 5 cm loop was made and 2.5 ml of a solution (Solution TJ, TK or TL), prepared above was administered. The solution remaining in the loop 90 minutes after the administration was collected.

The amount of protein (mg) in each collected solution that was released (eluted) from each rat large intestine was measured. The amount of released protein serves as a measure of damage of the large intestine.

The results were as follows:

Compared to Solution TJ (Control 4) that did not contain sodium laurate (solubilizer), Solution TK (Control 5) that contained sodium laurate (solubilizer) exhibited a significantly increased amount of protein released and the large intestines of the rats were damaged.

Compared to Solution TK (Control 5) that contained only sodium laurate (solubilizer), Solution TL (Example 3) that contained sodium laurate (solubilizer) and taurine suppressed the increase in elution of protein to about 1/4, and caused substantially no damage to the rat large intestine.

PREPARATION EXAMPLE P-1

Cilostazol bulk powder (800 g) ground by a jet mill and having an average particle diameter of about 2 $\mu$m, 800 g of hydroxypropylmethylcellulose, 224 g of D-mannitol, 60 g of sodium laurylsulfate (drug absorbefacient) and 60 g of spermine (product of Sigma-Aldrich Corporation) were mixed. The mixture was subjected to wet granulation by adding 900 g of purified water, dried and then sieved. To the sieved granules, 16 g of magnesium stearate (lubricant) was added and mixed. Using a punch having a diameter of 6.5 mm, the mixture was then subjected to tablet compression so that the weight of one tablet became 98 mg, producing tablets having a cilostazol content of 40 mg/tablet. The obtained tablets were placed into capsules in such a manner that each capsule held 5 tablets, and each multiple-unit type capsule had cilostazol content of 200 mg per capsule.

PREPARATION EXAMPLE P-2

Polyvinyl alcohol (3.3 g), mannitol (10 g), sodium laurylsulfate (2 g) and spermine (product of Sigma-Aldrich Corporation) (3 g) were dissolved in 106 g of water. To the obtained solution, 20 g of cilostazol bulk powder ground by a jet mill and having an average particle diameter of about 3 $\mu$m was dispersed and dissolved, and the obtained solution was subjected to spray drying to obtain a cilostazol powder preparation.

PREPARATION EXAMPLE P-3 (TABLET)

Rebamipide (20 g), 10 g of sodium taurocholate (product of TOKYO KASEI KOGYO CO., LTD.), 5 g of spermine (product of Sigma-Aldrich Corporation), 100 g of cornstarch (product of NIHON SHOKUHIN KAKO CO., LTD) and 100 g of crystalline cellulose (product of Asahi Kasei Corporation) were mixed, and 0.5 g of magnesium stearate (product of TAIHEI CHEMICALS LIMITED) was further added thereto. The thus obtained mixture was subjected to tablet compression using a punch having a diameter of 8.0 mm, producing tablets each weighting 235.5 mg.

PREPARATION EXAMPLE P-4 (TABLET)

Rebamipide (20 g), 10 g of sodium taurocholate (product of TOKYO KASEI KOGYO CO., LTD.), 10 g of spermine (product of Sigma-Aldrich Corporation), 100 g of cornstarch (product of NIHON SHOKUHIN KAKO CO., LTD) and 100 g of crystalline cellulose (product of Asahi Kasei Corporation) were mixed, and 0.5 g of magnesium stearate (product of TAIHEI CHEMICALS LIMITED) was further added thereto. The thus obtained mixture was subjected to tablet compression using a punch having a diameter of 8.0 mm, producing tablets each weighting 240.5 mg.

PREPARATION EXAMPLE P-5 (GRANULE)

Rebamipide (20 g), sodium taurocholate (product of TOKYO KASEI KOGYO CO., LTD.) (10 g), spermirie (product of Sigma-Aldrich Corporation) (10 g), cornstarch (product of NIHON SHOKUHIN KAKO CO., LTD) (100 g) and crystalline cellulose (product of Asahi Kasei Corporation) (100 g) were fed into a kneader (product of OKADA SEIKO CO., LTD., product name of NSK-150) and mixed, and 200 g of water was then added thereto to obtain a kneaded product. This kneaded product was subjected to extrusion granulation using an extrusion granulator equipped with a dome shaped die having openings of 0.8 mm (product of Fuji Paudal Co., Ltd., product name of Dome Gran DG-L1). The extrudates were spheronized into spherical shape using a spheronizer (product of Fuji Paudal Co., Ltd., product name of Marumerizer QJ-400). The thus obtained sieved pellets were dried, producing granules.

PREPARATION EXAMPLE P-6 (GRANULE)

Onto the granules obtained in Preparation Example P-5, a coating solution containing 6% hydroxypropylmethylcellulose, 2% polyethylene glycol, 1% talc and 1% titanium oxide was sprayed, producing coated granules.

PREPARATION EXAMPLE P-7 (SOLUTION

A mixture of 20 g of rebamipide, 10 g of sodium taurocholate (product of TOKYO KASEI KOGYO CO., LTD.), 10 g of spermine (product of Sigma-Aldrich Corporation), 100 g of hydroxypropylmethylcellulose (product of Shin-Etsu Chemical Co., Ltd.), 100 g of water and 0.5 ml of 2N-sodium hydroxide solution was heated at 37° C. and mixed until it became homogeneous, giving a solution.

PREPARATION EXAMPLE P-8 (SOLUTION)

A mixture of 20 g of rebamipide, 10 g of sodium taurocholate (product of TOKYO KASEI KOGYO CO., LTD.), 10 g of spermine (product of Sigma-Aldrich Corporation), 100 g of hydroxypropylmethylcellulose (product of Shin-Etsu Chemical Co., Ltd.), 100 g of water and 0.5 ml of 2N-sodium hydroxide solution was heated at 37° C. and mixed until the mixture became homogeneous, giving a solution.

PREPARATION EXAMPLE P-9 (SUPPOSITORY)

A mixture of 20 g of rebamipide, 150 g of Witepsol W-35 (product of SASOL Germany GmbH), 10 g of sodium taurocholate (product of TOKYO KASEI KOGYO CO., LTD.) and 10 g of spermine (product of Sigma-Aldrich Corporation) was heated at 37° C. and mixed until it became homogeneous. The thus obtained solution was placed in a mold to produce suppositories.

PREPARATION EXAMPLE P-10 (SUPPOSITORY)

A mixture of 20 g of rebamipide, 150 g of Witepsol H-15 (product of SASOL Germany GmbH), 10 g of sodium taurocholate (product of TOKYO KASEI KOGYO CO., LTD.) and 10 g of spermine (product of Sigma-Aldrich Corporation) was heated at 37° C. and mixed until it became homogeneous. The thus obtained solution was placed in a mold to produce suppositories.

PREPARATION EXAMPLE P-11 (SUPPOSITORY)

A mixture of 20 g of rebamipide, 150 g of polyethylene glycol 1000 (product of Sigma-Aldrich Corporation), 200 g of polyethylene glycol 4000 (product of Sigma-Aldrich Corporation), 100 g of water, 10 g of sodium taurocholate (product of TOKYO KASEI -KOGYO CO., LTD.) and 10 g of spermine (product of Sigma-Aldrich Corporation) was heated at 37° C. and mixed until it became homogeneous. The thus obtained solution was placed in a mold to produce suppositories.

PREPARATION EXAMPLE P-12 (SUPPOSITORY)

A mixture of 20 g of rebamipide, 150 g of polyethylene glycol 1000 (product of Sigma-Aldrich Corporation), 200 g of polyethylene glycol 8000 (product of Sigma-Aldrich Corporation), 100 g of water, 10 g of sodium taurocholate (product of TOKYO KASEI KOGYO CO., LTD.) and 10 g of spermine (product of Sigma-Aldrich Corporation) was heated at 37° C. and mixed until it became homogeneous. The thus obtained solution was placed in a mold to produce suppositories.

PREPARATION EXAMPLE P-13 (TABLET)

Spermine (product of Sigma-Aldrich Corporation) (5 g), 100 g of cornstarch (product of NIHON SHOKUHIN KAKO CO., LTD.) and 100 g of crystalline cellulose (product of Asahi Kasei Corporation) were mixed, and then 0.5 g of magnesium stearate (product of TAIHEI CHEMICALS LIMITED) was further added thereto. The obtained mixture was subjected to tablet compression using a punch having a diameter of 8.0 mm, producing tablets each weighting 225.5 mg.

PREPARATION EXAMPLE P-14 (GRANULE)

Spermine (product of Sigma-Aldrich Corporation) (10 g), cornstarch (product of NIHON SHOKUHIN KAKO CO., LTD) (100 g) and crystalline cellulose (product of Asahi Kasei Corporation) (100 g) were fed into a kneader (product of OKADA SEIKO CO., LTD., product name of NSK-150) and mixed, and then 200 g of water was then added thereto to obtain a kneaded product. This kneaded product was subjected to extrusion granulation using an extrusion granulator equipped with a dome shaped die having openings of 0.8 mm (product of Fuji Paudal Co., Ltd., product name of Dome Gran DG-L1). The extrudates were spheronized into spherical shape using a spheronizer (product of Fuji Paudal Co., Ltd., product name of Marumerizer QJ-400). The thus obtained pellets were dried, producing granules.

PREPARATION EXAMPLE P-15 (SOLUTION)

A mixture of 10 g of spermine (product of Sigma-Aldrich Corporation), 100 g of hydroxypropylmethylcellulose (product of Shin-Etsu Chemical Co., Ltd.), 100 g of water and 0.5 ml of 2N-sodium hydroxide solution was heated at 37° C. and mixed until it became homogeneous, giving a solution.

PREPARATION EXAMPLE P-16 (SUPPOSITORY)

A mixture of 150 g of Witepsol W-35 (product of SASOL Germany GmbH) and 10 g of spermine (product of Sigma-Aldrich Corporation) was heated at 37° C. and mixed until the mixture became homogeneous. The thus obtained solution was placed in a mold to produce suppositories.

PREPARATION EXAMPLE P-17 (SUPPOSITORY)

A mixture of 150 g of polyethylene glycol 1000 (product of Sigma-Aldrich Corporation), 200 g of polyethylene glycol 4000 (product of Sigma-Aldrich Corporation), 100 g of water and 10 g of spermine (product of Sigma-Aldrich Corporation) was heated at 37° C. and mixed until it became homogeneous. The thus obtained solution was placed in a mold to produce suppositories.

PREPARATION EXAMPLE P-18 (SUPPOSITORY)

A mixture of 150 g of polyethylene glycol 1000 (product of Sigma-Aldrich Corporation), 200 g of polyethylene glycol 8000 (product of Sigma-Aldrich Corporation), 100 g of water and 10 g of spermine (product of Sigma-Aldrich Corporation) was heated at 37° C. and mixed until it became homogeneous. The thus obtained solution was placed in a mold to produce suppositories.

TEST EXAMPLE P-1

Using phenol red (PR) as a model compound for testing absorption, the following 7 kinds of solutions were prepared:

Solution PA (Control 6)

PR was added to tris-hydrochloric acid buffer solution (pH 7.4) until the concentration of PR became 100 $\mu$M, giving Solution PA.

Solution PB (Control 7)

PR and spermine (polyamine) were added to tris-hydrochloric acid buffer solution (pH 7.4) so that the concentration of PR became 100 $\mu$M and that of spermine became 10 mM, giving Solution PB.

SOLUTION PC (COMPARATIVE EXAMPLE 5)

PR and sodium taurodeoxycholate (solubilizer) were added to tris-hydrochloric acid buffer solution (pH 7.4) so that the concentration of PR became 100 $\mu$M and that of sodium taurodeoxycholate became 5 mM, giving Solution PC.

SOLUTION PD (COMPARATIVE EXAMPLE 6)

PR and sodium taurodeoxycholate (solubilizer) were added to tris-hydrochloric acid buffer solution (pH 7.4) so that the concentration of PR became 100 $\mu$M and that of sodium taurodeoxycholate became 0.5 mM, giving Solution PD.

SOLUTION PE (EXAMPLE 4)

PR, sodium taurodeoxycholate (solubilizer) and spermine (polyamine) were added to tris-hydrochloric acid buffer solution (pH 7.4) so that the concentration of PR became 100 $\mu$M, that of sodium taurodeoxycholate became 0.5 mM and that of spermine became 10 mM, giving Solution PE.

Solution PF (Control 8)

PR and sodium laurate (solubilizer) were added to tris-hydrochloric acid buffer solution (pH 7.4) so that the concentration of PR became 100 μm and that of sodium laurate became 2 mM, giving Solution PF.

SOLUTION PG (EXAMPLE 5)

PR, sodium laurate (solubilizer) and spermine (polyamine) were added to tris-hydrochloric acid buffer solution (pH 7.4) so that the concentration of PR became 100 μm, that of sodium laurate became 2 mM and that of spermine became 10 mM, giving Solution PG.

(1) Test Conducted Using Sodium Taurodeoxycholate as a Solubilizer

SD male rats (body weight of about 250 g) were used as test animals. In the upper part of the large intestine of each rat, a 5 cm loop was made and 2.5 ml of a solution (Solution PA, PB, PC, PD or PE), prepared above was administered. The solution remaining in the loop 1.5 hours after the administration was collected. The residual amount of PR in each collected solution was measured to obtain the absorption rate of PR (%) absorbed in the large intestine of each rat.

The amount of protein (mg) in each collected solution that was released (eluted) from the large intestine of each rat was also measured. The amount of released protein is a marker of damage of the large intestine.

Table 3 shows the results.

TABLE 3

| Solution | PR absorption rate (%) | Amount of protein released (mg) |
| --- | --- | --- |
| PA (Control 6) | 9.2 ± 0.9 | 0.36 ± 0.07 |
| PB (Control 7) | 10.3 ± 1.8 | 0.28 ± 0.09 |
| PC (Comparative Example 5) | 38.4 ± 1.4 | 2.22 ± 0.26 |
| PD (Comparative Example 6) | 5.4 ± 1.4 | 0.22 ± 0.04 |
| PE (Example 4) | 22.4 ± 1.2 | 0.48 ± 0.04 |

Each figure in table 3 indicates the mean value ±S.E. of 4–11 rats.

Table 3 indicates the following:

Both Solution PB (Control 7) that contained spermine (polyamine), and Solution PA (Control 6) that did not contain spermine (polyamine) exhibited substantially no difference in absorption rate of PR and almost the same level of protein elution. Therefore, it is clear that spermine itself does not affect the absorption of pharmacologically active substances nor the mucous membrane of rat large intestine.

Compared to Solution PA (Control 6) that did not contain sodium taurodeoxycholate (solubilizer) and Solution PB (Control 7) that contained spermine (polyamine), Solution PD (Comparative Example 6) that contained a low concentration of sodium taurodeoxycholate (solubilizer) exhibited lower absorption rate of PR; however, the amount of released protein was not significantly different between the three. It is assumed that the reason that the absorption rate of PR was decreased by Solution PD is that PR was uptaken by the micelles formed by sodium taurodeoxycholate (solubilizer), so that the PR was thereby not absorbed in the intestinal tract.

Compared to Solution PD (Comparative Example 6) that contained a low concentration of sodium taurodeoxycholate (solubilizer), Solution PC (Comparative Example 5) that contained a high concentration of sodium taurodeoxycholate (solubilizer) improved the absorption rate of PR; however, it significantly increased the amount of protein released and the large intestines of the rats were damaged.

Solution PE (Example 4) that contained a low concentration of sodium taurodeoxycholate (solubilizer) and spermine (polyamine) significantly improved the absorption rate of PR and had almost no adverse affect on the amount of protein released, and therefore it did not damage the large intestines of the rats.

(2) Test Conducted Using Sodium Laurate as a Solubilizer

SD male rats (body weight of about 250 g) were used as test animals. In the upper part of the large intestine of each rat, a 5 cm loop was made and 2.5 ml of the solution (Solution PA, PB, PC, PD or PE), prepared above was administered. The solution remaining in the loop 1.5 hours after the administration was collected.

The residual amounts of PR in each collected solution were measured to obtain the absorption rate of PR (%) absorbed in the large intestine of each rat.

The amount of protein (mg) in each collected solution that was released (eluted) from the large intestine of each rat was also measured. The amount of released protein is a marker of the damage of the large intestine.

Table 4 shows the results.

TABLE 4

| Solution | PR absorption rate (%) | Amount of protein released (mg) |
| --- | --- | --- |
| PA (Control 6) | 9.2 ± 0.9 | 0.36 ± 0.07 |
| PF (Control 8) | 17.6 ± 2.0 | 1.42 ± 0.20 |
| PG (Example 5) | 25.3 ± 1.1 | 0.69 ± 0.06 |

Each figure in table 4 indicates the mean-value ±S.E. of 4–11 rats.

Table 4 indicates the following:

Compared to Solution PA (Control 6) that did not contain sodium laurate (solubilizer), Solution PF (Control 8) that contained sodium laurate (solubilizer) improved the absorption rate of PR; however, it significantly increased the amount of protein released and the large intestines of rates were damaged.

Compared to Solution PF (Control 8) that contained only sodium laurate (solubilizer), Solution PG (Example 5) that contained both spermine (polyamine) and sodium laurate (solubilizer) improved the absorption rate of PR and had almost no adverse affect on the amount of protein released, and therefore it did not damage the large intestines of the rats.

As is clear from the results shown in tables 3 and 4, when a low concentration of solubilizer is used, by adding a solubilizer and polyamine to the medicinal composition, it becomes possible to achieve almost the same or better drug absorption enhancing effect as in the case where a solubilizer is used in such a high concentration that it damages the intestinal mucosa, thus increasing the safety.

TEST EXAMPLE P-2

Using rebamipide (product name of Mucosta, product of Otsuka Pharmaceutical Co., Ltd.) as a model compound for testing absorption, the following four kinds of solutions were prepared.

Solution PH (Control 9)

Rebamipide and hydroxypropylmethylcellulose (product name of TC-5E, product of Shin-Etsu Chemical Co., Ltd.) were added to tris-hydrochloric acid buffer solution (pH 7.4) so that the concentration of rebamipide became 2.0 mg/ml and that of hydroxypropylmethylcellulose became 1 wt. %; 2N—NaOH was then added thereto dropwise so as to convert the mixture into a solution state, giving Solution PH.

Solution PI (Control 10)

Rebamipide, hydroxypropylmethylcellulose and sodium taurocholate (solubilizer) were added to tris-hydrochloric acid buffer solution (pH 7.4) so that the concentration of rebamipide became 2.0 mg/ml, that of hydroxypropylmethylcellulose became 1 wt. % and that of sodium taurocholate became 5 mM, 2N—NaOH was then added thereto dropwise so as to convert the mixture into a solution state, giving Solution PI.

SOLUTION PJ (EXAMPLE 6)

Rebamipide, hydroxypropylmethylcellulose, sodium taurocholate (solubilizer) and spermine (polyamine) were added to tris-hydrochloric acid buffer solution (pH 7.4) so that the concentration of rebamipide became 2.0 mg/ml, that of hydroxypropylmethylcellulose became 1 wt. %, that of sodium taurocholate became 5 mM and that of spermine became 10 mM, 2N—NaOH was then added thereto dropwise so as to convert the mixture into a solution state, giving Solution PJ.

SOLUTION PK (EXAMPLE 7)

Rebamipide, hydroxypropylmethylcellulose and spermine (polyamine) were added to tris-hydrochloric acid buffer solution (pH 7.4) so that the concentration of rebamipide became 2.0 mg/ml, that of hydroxypropylmethylcellulose became 1 wt. % and that of spermine became 10 mM; 2N—NaOH was then added thereto dropwise so as to convert the mixture into a solution state, giving Solution PJ.

SD male rats (body weight of about 250 g) were used as test animals. In the upper part of the large intestine of each rat, a 5 cm loop was made and 2.5 ml of a solution (Solution PH, PI, PJ or PK) prepared above were administered. Blood was collected from the jugular vein of the rats 5 minutes, 15 minutes, 30 minutes, 45 minutes, 60 minutes and 90 minutes after administration. The solution remaining in the loop 90 minutes after the administration was then collected.

Total absorbed amounts of rebamipide (ng.hr/ml) over 90 minutes from the administration were measured and shown in table 5 as $AUC_{1.5\ hr}$. The maximum concentrations of rebamipide in blood (ng/ml) 5–90 minutes after the administration were measured and shown in table 5 as $C_{max}$. The amount of the phospholipid released (eluted) from the large intestines of the rats was measured and shown in table 5.

TABLE 5

| Solution | $AUC_{1.5hr}$ (ng · hr/ml) | $C_{max}$ (ng/ml) | Amount of phospholipid released ($\mu$g) |
|---|---|---|---|
| PH (Control 9) | 1169 ± 162 | 1155 ± 204 | 97.6 ± 2.2 |
| PI (Control 10) | 848 ± 151 | 742 ± 166 | 93.6 ± 0.5 |
| PJ (Example 6) | 7249 ± 1160 | 6581 ± 864 | 111.7 ± 2.7 |
| PK (Example 7) | 3017 ± 303 | 3403 ± 527 | 106.8 ± 2.2 |

Each figure in table 5 indicates the mean value ±S.E. of 4 rats.

Table 5 indicates the following:

Compared to Solution PH (Control 9) that did not contain sodium taurocholate (solubilizer), Solution PI (Control 10) that contained a low concentration of sodium taurocholate (solubilizer) decreased the absorption rate of rebamipide; however, it made almost no difference to the dissolution amount of phospholipid. It is assumed that the reason that the absorption rate of rebamipide decreased is that rebamipide was uptaken by the micelle formed by sodium taurocholate (solubilizer), and the rebamipide was thereby not absorbed in the intestinal tract.

Solution PJ (Example 6) containing a low concentration of sodium taurocholate (solubilizer) and spermine (polyamine) remarkably improved the absorption rate of rebamipide and had almost no adverse affect on the dissolution amount of phospholipid, and therefore it did not damage the large intestine of rats.

Solution PK (Example 7) that contained spermine (polyamine) increased the absorption of rebamipide. In the above-described Test Example P-1, when spermine (polyamine) was used with PR, a PR absorption-enhancing effect was not observed, and therefore it became clear that spermine (polyamine) specifically affects poorly soluble pharmacologically active substances and exhibits an absorption-enhancing effect.

When cilostazol instead of the rebamipide was used in Solution PK of Example 7, similar results to those as described above were obtained.

Furthermore, when polyamines other than the spermine were used in solution PK of example 7, similar results to those described above were obtained.

What is claimed is:

1. A medicinal composition comprising a pharmacologically active substance, a drug absorbefacient and a taurine compound.

2. The medicinal composition according to claim 1, wherein the pharmacologically active substance is at least one member selected from the group consisting of theophylline, cilostazol, grepafloxacin, carteolol, procaterol, rebamipide, aripiprazole, 5-fluorouracil, diclofenac, cyclosporin, nifedipine, phenol red, Tolvaptan, interferon-α, interferon-β, vesnarinone, nadifloxacin, Toborinone, pranidipine, cefazolin, buprenorphine, probucol, γ-oryzanol, 1-[3-[4-(3-chlorophenyl)-1-piperazinyl]propyl]-5-methoxy-3,4-dihydro-2(III)-quinolinone monomethane sulfonate, 4-(N-methyl-2-pheriylethylamino)-1-(3,5-dimethyl-4-propionylaminobenzoyl)piperidine hydrochloride monohydrate, (±)-5-dimethylamino-1-[4-(2-methylbenzoylamino)benzoyl]-2,3,4,5-tetrahydro-1H-benzazepine hydrochloride, 6-[2-(3,4-diethoxyphenyl) thiazol-4-yl]pyridine-2-carboxylic acid, mevalotin, loxonin, Blopress, Basen, Takepron, Pansporin, Certa, Calslot Norvasc, Lipitor, Cardenalin, Viagra, Cravit, Panaldine, Gaster, Hamal, Perdipine, Selbex, Glakay, Aricept, Lipovas, Nu-Lotan, Renivace, Flomox, Flumarin, Kefral, Zaditen, Lamisil, Epogin, Cefzon, Intal and Nivadil.

3. The medicinal composition according to claim 1, wherein the drug absorbefacient is at least one member selected from the group consisting of alkali metal salts or bile acids and alkali metal salts of $C_{6-20}$ fatty acids.

4. The medicinal composition according to claim 3, wherein the drug absorbefacient is at least one member selected from the group consisting of alkali metal salts of taurocholic acid and alkali metal salts of lauric acid.

5. The medicinal composition according to claim 1, wherein the taurine compound is taurine.

6. A composition comprising an intestinal musoca protective agent in combination with a medicinal composition, wherein the intestinal mucosa protective agent comprises a taurine compound, and wherein the medicinal composition comprises a pharmacologically active substance and a drug absorbefacient.

7. The composition according to claim 6, wherein the taurine compound is taurine.

8. A method for suppressing or preventing damage of the intestinal mucosa caused by a drug absorbefacient comprising administering to a patient in need thereof medicinal composition containing a pharmacologically active substance and a drug absorbefacient, together with an intestinal mucosa protective agent comprising a taurine compound, thereby suppressing or preventing damage of the intestinal mucosa caused by a drug absorbefacient in said patient.

9. A method for suppressing or preventing damage of the intestinal mucosa caused by administrating a medicinal composition that contains a pharmacologically active substance and a drug absorbefacient, the method comprising administering a taurine compound to a patient in need of such suppression or prevention of damage of the intestinal mucosa.

10. A method for producing a composition that suppresses or prevents damage of intestinal mucosa, said method comprises combining, an intestinal mucosa protective agent with a medicinal composition, wherein said intestinal mucosa protective agent is a taurine compound, and wherein said medicinal composition comprises a pharmacologically active substance and a drug absorbefacient.

* * * * *